United States Patent [19]

Cox

[11] Patent Number: 4,969,899
[45] Date of Patent: Nov. 13, 1990

[54] INFLATABLE IMPLANT

[75] Inventor: James E. Jr. Cox, Oxnard, Calif.

[73] Assignee: Cox-Uphoff International, Carpinteria, Calif.

[21] Appl. No.: 320,358

[22] Filed: Mar. 8, 1989

[51] Int. Cl.$^5$ .............................................. A61F 2/12
[52] U.S. Cl. .................................................... 623/8
[58] Field of Search ........................................... 623/8

[56] References Cited

U.S. PATENT DOCUMENTS

| | | | |
|---|---|---|---|
| 3,600,718 | 8/1971 | Boone | 623/8 |
| 3,752,162 | 8/1973 | Newash | 623/66 |
| 3,913,587 | 10/1975 | Newash | 623/66 |
| 4,264,990 | 5/1981 | Hamas | 623/8 |
| 4,636,213 | 1/1987 | Pakiam | 623/8 |
| 4,643,733 | 2/1987 | Becker | 623/8 |
| 4,662,883 | 5/1987 | Bell et al. | 623/8 |
| 4,775,379 | 10/1988 | Fogarty et al. | 623/8 |

Primary Examiner—Randall L. Green
Assistant Examiner—Stephanie L. Iantorno
Attorney, Agent, or Firm—Donald D. Mon

[57] ABSTRACT

An inflatable implant has a flexible shell that forms an internal lumen. It has a base portion and an envelope portion, with an aperture through the base. A tubing storage shell is in the lumen and attached to the base, forming a peripheral seal with the base around the aperture in the base. A flexible fill tubing is structurally permanently attached to the tubing storage shell, sealed with the aperture in the tubing storage shell and passing freely through the aperture in the base. A substantial length of the fill tubing is stored in the storage shell which can be drawn toward an incision in the skin of the patient so the volume of the implant can be adjusted without directly accessing the shell.

7 Claims, 2 Drawing Sheets

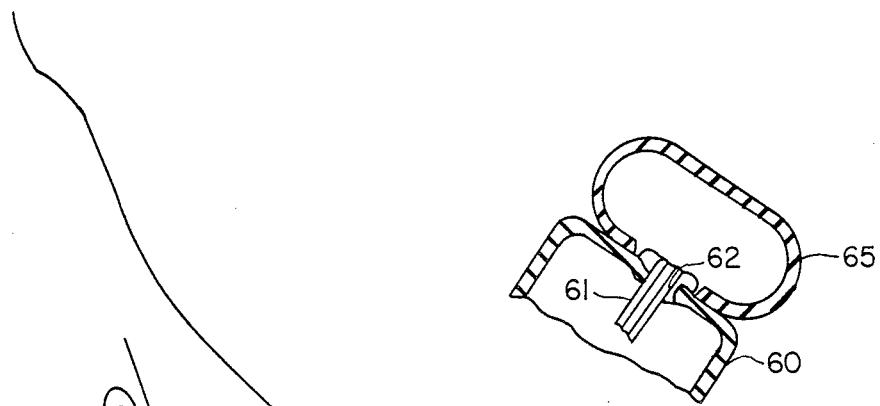
FIG. 3
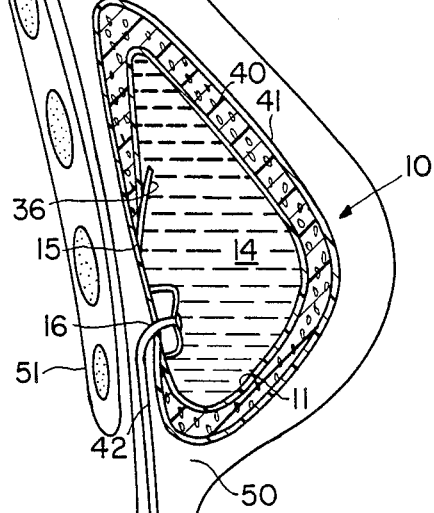
FIG. 2
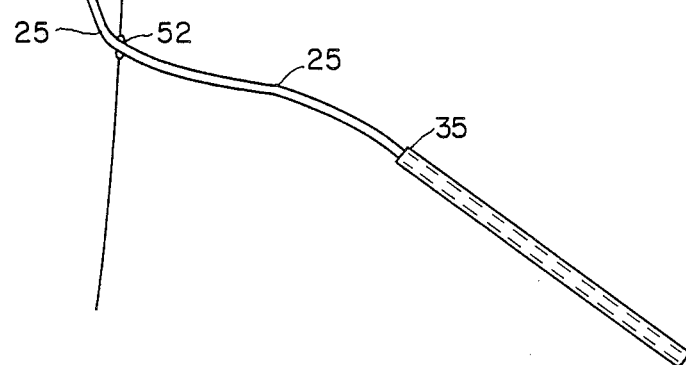

INFLATABLE IMPLANT

FIELD OF THE INVENTION

This invention relates to inflatable prosthetic implants used to replace excised tissue, to augment existing tissues and configurations, or to be used as tissue expanders.

BACKGROUND OF THE INVENTION

Fluid filled prostheses are widely used to replace excised tissue, for example after a radical mastectomy, or to augment it to improve surface configurations. Examples of both of these are regularly encountered in the field of cosmetic and reconstructive surgery. Although there are many applications where these are used, the most common is the mammary prosthesis, used to change the size or shape of the female breast. These are relatively long-lived applications, and are conventionally referred to as "prostheses".

There is yet another type of inflatable implant, which is typified in Radovan U.S. Pat. No. 4,217,889. The objective of this type of implant is to expand the skin by enlarging an implant underneath it. Then when the implant is removed, a longer surface length of skin remains, which can be used as a flap next to a burn site, for example. Other uses include advancing the hairline of a bald person. These implants are not properly called prostheses due to the short term of their usage, but they both can advangtageously use this invention. They will both be referred to herein as "inplants".

Many or even most implants are manufactured to a given size and shape, and are implanted without means or expectation of changing their size after implantation. However, in many situations it is desirable to be able to adjust the size over a substantial period of time. If the volume can later be adjusted, an implant of lesser initial volume can be implanted, and as the post-surgical swelling goes down, the implant used as a prosthesis can be enlarged. Also, because often the procedure is for cosmetic purposes, it is useful to be able to make a later adjustment of size without having to replace the prosthesis with one of a different size, which would require a subsequent surgical procedure. A useful example of an adjustable prosthesis is shown in Becker U.S. Pat. No. 4,643,733, issued Feb. 17, 1987.

A problem with the adjustable implants known to the instant inventor is that they require a normally-closed valve to be part of the implant itself to retain fluid in the implant once it is filled and to hold it so long as the implant is in place.

While implants of this type are quite durable and are not usually subjected to hard forces, still especially prosthetic implants are left in place for many years, and must also stand up to occasional rough usage. Furthermore the available materials of construction are limited because they are implanted, and some of these materials do permit long-term leaking out of fluids. As a consequence, gradual leakage over a period of time, or even relatively abrupt loss of fluid sometimes occurs, and this requires surgical techniques to replace the fluid or to replace the prosthesis.

The principal problem is in the fill valve itselt, which sometimes leaks. It is an object of this invention to provide an adjustable volume implant which does not require a fill valve at all, and in which, if for some reason more or less fluid is needed in the implant, the adjustment can be accomplished through a minor local surgical incision through the skin, without requiring direct access to the body of the inplant itself. Truly invasive surgery is not needed.

BRIEF DESCRIPTION OF THE INVENTION

An inflatable implant according to this invention includes a flexible first shell that forms an internal lumen to receive and retain fluid. This shell has a base portion and a bonnet portion to form the lumen. An aperture passes through the base portion into the lumen.

A tubing storage shell is disposed inside this lumen. It is substantially impermeable, and makes a peripheral seal with the base portion around the aperture. It has an internal cavity, and its wall has an aperture opening into the lumen.

A flexible fill tubing is sealingly fitted in the aperture in the tubing storage shell. Thus the fill tubing gives access to the lumen, but otherwise closes the lumen. A substantial length of fill tubing is initially disposed in the cavity, and passes out of the shell through the aperture in the base.

The lumen is usually empty while the implant is being implanted, because this requires a smaller incision. Then there usually is a valve through which the lumen is quickly filled to an approximate size. The valves used for this quick-fill purpose are generally quite large and function well, but they are not suited for a later size adjustment function.

When the instant implant is implanted, some of the fill tubing extends out of the tubing storage shell and is led to an incision through the skin. This incision can actually be located quite far from the implant itself. A fill reservoir is connected to the fill tubing. It has a selt-sealing surface which can be pierced by a syringe needle, and fluid can thereby by injected into or withdrawn from the lumen through the fill tubing. The reservoir is placed subcutaneously. It forms a closed system with the implant. After the incision is closed, adjustment of volume can be accomplished by penetrating the skin and the dome of the fill reservoir with a hypodermic needle, and fluid is injected into the reservoir (and thereby into the prosthesis) or removed from it is desired.

The fill tubing is best made extremely thin, and could tend to kink during implantation and initial usage. For this reason that part of it which initially extends out of the shell will be contained in a reinforcing tube that is loosely attached to the prosthesis so it can easily by pulled loose. The reinforcing tube will be removed when the adjustments are completed.

After the volume is adjusted to its ultimately desired size, the incision is opened and the fill reservoir is pulled out. Also, as shown in FIG. 2, the reinforcing tube will be pulled out and off of the fill tubing. The excess length of fill tubing that is still in the tubing storage shell is pulled out so there is a minimum length of tubing between the aperture in the shell and the incision. The fill tubing is then cut to length and tied off or otherwise occluded at the incision. The incision is closed over the end of the fill tubing. The fill system is thereby closed without valving.

Should later adjustment be needed, the end of the fill tubing can be located and pulled out through a local incision, and connected again to means for injecting or removing fluid. Access to the implant itself is not needed.

The above and other features of this invention will be fully understood from the following detailed description and the accompanying drawings, in which:

BRIEF DESCRIPTION OF THE DRAWINGS:

FIG. 2 illustrates the method of using the invention;

FIG. 3 is a fragmentary cross-section showing another embodiment of the invention.

DETAILED DESCRIPTION OF THE INVENTION

Figure 1:
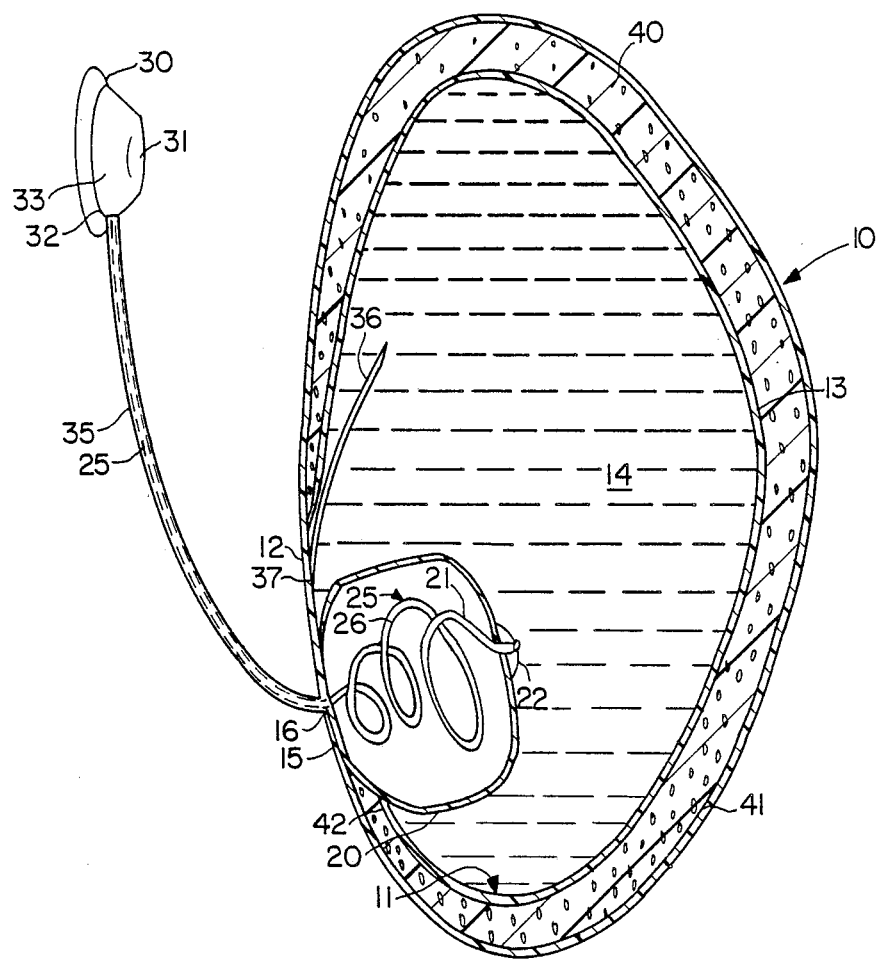
FIG. 1 is a semi-schematic cross-section of the presently-preferred embodiment of the invention.

FIG. 1 is a semi-schematic cross-section of the presently-preferred embodiment of an implant according to the invention. The illustrated embodiment is a mammary prosthesis. It is a double-lumen type, in which two separate lumens contain two different fluids. The term "fluid" herein means any liquid, or semi-liquid such as a gel having little shear strength so as to respond readily to such forces on the prosthesis as squeezing or other compressive or displacement forces. In the outer lumen it is common to place medical grade silicone gel (a semi-liquid). This gel is well-known, and provides good tactile response in the sense of simulating tissue response to external forces. The inner lumen is usually filled with normal saline solution, and the volume of this lumen is adjusted to established the ultimate volume of the prosthesis.

It should be understood that the outer lumen is optional. A sigle lumen prosthesis is also useful.

Prosthesis 10 has a flexible first shell 11. The shell includes a base 12 and a bonnet 13. These are actually formed as a single piece on a mandrel by a dipping process. The base is relatively flat, and the bonnet is bulb shaped. Together they form a first lumen 14.

A reinforced path 15 forms part of the base, and has an aperture 16 through it.

A tubing storage shell 20 is disposed inside the lumen. It may be somewhat rigid so as to be less likely to become fully compressed, or if preferred may be quite flexible. Whichever the situation, it is generally circular and impermeable to fluids to be contained in the lumen. It makes a fluid tight seal with the shell around aperture 16. It has an aperture 21 which opens into the lumen. Conveniently, there will be a button shaped reinforcement 22 through which this aperture passes. This facilitates making a fluid-tight connection with one end of a flexible fill tubing 25.

Tubing 25 has excess length 26 coiled in the storage shell, and which leads out of the prosthesis through aperture 16. It may or may not make a fluid seal with aperture 16. This is immaterial. In any event it is slidable in aperture 16.

Tubing 25 extends to a fill reservoir 30, which is a hollow closed body with a surface 31 that is self-sealing after being punctured by the needle of a syringe. A port 32 extends from its cavity 33 to connect to tubing 25. Thus, fluid injected into or removed from cavity 33 is directly equal to flud added to or removed from the lumen.

Usually about a few inches of tubing will be stored in the storage shell, and another few inches will extend out of it. This will be enough for most practical procedures.

Fill tubing 25 has a thin wall section and as a small a bore as possible. Therefore it is subject to being kinked except in the storage shell where it is protected. To minimize this risk, reinforcement tube 35 receives and surrounds the fill tubing. It will be lightly attached to the reinforcement patch so it can be pulled loose and off of the fill tubing afte the implantation and volume adjustment have been initially concluded. The small size of the fill tube imposes least stress on the surrounding tissue.

Injection or removal of fluid through tubing 25 to adjust the size of the implant, can be continued or repeated long after the surgical implantation has been completed. Because the bore is small, this will be a relatively slow procedure. However, a first partial filling is done during the surgical procedure of implantation. Here speed is important. For this reason a quick-fill valve 36 is fitted in a slit 37 through the base. It is a normally-closed valve of the "Bronx Cheer" type. It is opened by a fill tube (not shown), and returns to its closed position when the fill tube is removed. A valve of this type is shown in Cox U.S. Pat. No. 4,178,643, issued Dec. 18, 1979 which is incorporated herein by reference in its entirety for its showing of valve 35. It is not used for filling after the initial implantation procedure.

In the preferred embodiment, a second lumen 40 surrounds the bonnet and perhaps part of the base. It is formed by a second shell 41. Shell 41 makes a peripheral sealing attachment 42 around aperture 16, or more precisely on the base or on the reinforcement patch. Lumen 40 is filled with a medical grade silicone gel by the use of known manufacturing techniques. Again, the second shell is optional. A single shell without it constitutes a viable and useful implant, and will commonly be used for a tissue expander, where a gel-filled lumen would serve no purpose.

The implantation of the implant of FIG. 1 is straightforward. With the gel already in lumen 40, and the inner lumen empty, it is inserted into a surgically prepared pocket 50 (FIG. 2). This pocket for mammary prostheses is outside of the rib cage 51. For access an incision 52 is cut at an acceptable location. After implantation, the inner lumen will be partially filled with normal saline solution through the quick fill valve. The reinforcement tubing and the length of fill tubing it encloses will be led out to the incision. The subsequent adjustment of the volume will be done through the reservoir. At this time the reinforcement tubing remains connected to the prosthesis and to the reservoir, and the reservoir is beneath the closed incision. After the volume is satisfactorily adjusted, which requires days or weeks, the incision will be opened. The reservoir and reinforcement tubing will be pulled off of the prosthesis and the fill tubing, and the reserved fill tubing will be pulled out of the storage shell. The fill tubing will be cut off to length at the incision and occluded, perhaps by a means as simple as a knot tied in it. The closed end is placed beneath the skin and the incision is again closed. Now the prosthesis is in place, and the fill tubing is closed. There is no problem with a valve, because there is no valve. The small bore tubing will cause no problem in situ. All of the structures are made of material which can be tolerated by human tissue over a long period of time. Medical grade silicones, polyethylene, and polyurethane are well-known materials.

Should a later adjustment be needed, the end of the tubing can readily be located. Tubing 25 can advantageously be made of radio-opaque material so it can readily be found. Then an incision will be made to give access to it. Fluid can be injected into the tubing or removed from it as desired or a reservoir could again be connected to it as desired. After this adjustment is made, the fill tubing will again be occluded and the incision closed. The use of the invention as a tissue expander is similar.

FIG. 3 shows another means to make a useful single lumen implant which includes the advantages of this invention. It can be used as a prosthesis or as a tissue expander. For brevity it shows only a tubing storage shell 60 identical to shell 20. An inner shell identical to shell 11 is formed around it. A fill tubing 61 identical to fill tubing 25 is fluidly sealed in an aperture 62 in the tubing storage shell. This embodiment differs from that of FIGS. 1 and 2 only in having but one shell (outside of the tubing storage shell) and in having in addition an inflatable balloon 65 which is sealed to shell 60 (or if preferred to shell 20) and in communication with the fill tubing.

With this arrangement a convenient all-saline adjustable implant can be provided, the adjustment being made by changing the volume of the ballon. Alternatively, lumen 14 could be filled with a gel, and adjustment of the implant's volume made by injecting or removing saline solution from the ballon.

This invention is not to be limited by the embodiments shown in the drawings and described in the description, which are given by way of example and not of limitation, but only in accordance with the scope of the appended claims.

I claim:

1. An inflatable implant comprising:
   a flexible shell forming an internal lumen to receive and to retain fluid, said shell having a base portion and an envelope portion to form said lumen, said base portion having an aperture therethrough;
   a tubing storage shell in said lumen attached to said base and forming a peripheral seal with the base around the aperture, said tubing storage shell having an internal cavity and an aperture opening into said lumen; and
   a flexible fill tubing having first and second ends and inner and outer surfaces, said outer surface of said first end structurally permanently sealed within the aperture of said tubing storage shell, said second end passing through the aperture in said base, said internal cavity being so proportioned and arranged as to received and to store a substantial length of said fill tubing, whereby after implanation of said implant, some of said fill tubing can be withdrawn from said internal cavity and drawn toward an incision in the skin of the patient, and whereby fluid can be injected or withdrawn through said fill tubing, and after the desired quantity of fluid is in the lumen, the fill tubing can be occluded at a location spaced from the shell, thereby retaining fluid in the lumen without requiring a valve to retain it therein, and providing a convenient point of access to said fill tube to adjust the volume of fluid in the shell.

2. An implant according to claim 1 in which a normally closed fill valve extends through said base into said lumen to enable more rapid initial filling of the lumen.

3. An implant according to claim 1 and further comprising a fill reservoir having self-sealing puncturable surface and an inside cavity, said reservoir being attached to said second end of said fill tubing, with said inside cavity in fluid communication with said fill tubing, whereby fluid can be injected into said fill reservoir and thence be conveyed to said lumen through said fill tubing.

4. An implant according to claim 1 in which the base includes a reinforced patch in which said aperture is located, and to which said tube storage shell is attached.

5. An implant according to claim 1 in which a reinforcement tube is releasably attached to said base at said aperture, said fill tubing passing through said rainforcement tube said reinforcement tube protecting said fill tubing from kinking.

6. An implant according to claim 1 in which an inflatable balloon sealingly fits around the aperture of said base portion whereby to receive fluid to change its volume and thereby to change the volume of the prosthesis.

7. An implant according to claim 1 in which a second flexible shell substantially surrounds said first flexible shell, sealing with said first shell around said aperture of said base portion, whereby to form a second lumen which is located between said shells.

* * * * *